(12) United States Patent
Lasley et al.

(10) Patent No.: US 8,703,751 B2
(45) Date of Patent: Apr. 22, 2014

(54) ANDROSTENEDIOL AS AN INDICATOR FOR ASSESSING ESTROGENICITY

(75) Inventors: William L. Lasley, Inverness, CA (US); Daniel S. McConnell, Ann Arbor, MI (US); Nancy A. Gee, Woodland, CA (US); Jiangang Chen, Knoxville, TN (US)

(73) Assignees: The Regents of the University of California, Oakland, CA (US); The Regents of the University of Michigan, Ann Arbor, MI (US)

( * ) Notice: Subject to any disclaimer, the term of this patent is extended or adjusted under 35 U.S.C. 154(b) by 17 days.

(21) Appl. No.: 13/508,008

(22) PCT Filed: Nov. 9, 2010

(86) PCT No.: PCT/US2010/055967
§ 371 (c)(1),
(2), (4) Date: Jul. 18, 2012

(87) PCT Pub. No.: WO2011/057241
PCT Pub. Date: May 12, 2011

(65) Prior Publication Data
US 2012/0277203 A1 Nov. 1, 2012

Related U.S. Application Data

(60) Provisional application No. 61/259,422, filed on Nov. 9, 2009.

(51) Int. Cl.
*A61K 31/56* (2006.01)
(52) U.S. Cl.
USPC .......................................... 514/170; 514/182

(58) Field of Classification Search
USPC .................................................. 514/170, 182
See application file for complete search history.

(56) References Cited

U.S. PATENT DOCUMENTS 5,641,768 A 6/1997 Loria

FOREIGN PATENT DOCUMENTS

WO WO9856386 12/1998

OTHER PUBLICATIONS

Reed et al., Journal of Steroid Biochemistry, 1988;30:489-492.*
Adams, et al., "Estrogenic effects of physiological concentrations of 5-androstene-3 beta, 17 beta-diol and its metabolism in MCF7 human breast cancer cells," *Cancer Res.* (1981) 41(11 Pt 1):4720-6.
Crawford, et al., "Circulating Dehydroepiandrosterone Sulfate Concentrations during the Menopausal Transition," *J Clin Endocrinol Metab* (2009) 94: 2945-2951.
Lasley, et al., "Circulating Dehydroepiandrosterone Sulfate Levels in Women with Bilateral Salpingo-Oophorectomy during the Menopausal Transition," *Menopause.* (2011) 18(5): 494-498.
PCT Declaration of Non-Establishment of International Search Report for Application No. PCT/US2010/055967, mailed Jul. 19, 2011, 2 pages total.
Santoro, et al., "Correlates of Circulating Androgens in Mid-Life Women: The Study of Women's Health Across the Nation," *J Clin Endocrinol Metab.* (2005) 90(8):4836-45.

(Continued)

*Primary Examiner* — San-Ming Hui
(74) *Attorney, Agent, or Firm* — Jennifer L. Wahlsten; Weaver Austin Villeneuve & Sampson LLP

(57) ABSTRACT

The present invention provides methods of determining whether a female patient will benefit from hormone replacement therapy.

23 Claims, 11 Drawing Sheets

(56) References Cited

OTHER PUBLICATIONS

Segal, Sheldon J. and Luigi Mastorianni 2003. "Hormone Use in Menopause & Male Andropause," Oxford. pp. 87-88.

Sowers, et al., Levels of Sex Steroid and Cardiovascular Disease Measures in Premenopausal and Hormone-Treated Women at Midlife *Arch Intern Med.* (2008) 168(19):2146-2153.

\* cited by examiner

*Figure 3*

Only DS and A-diol have a significant increase...

| Characteristic | Baseline DHEAS Baseline Profile 1 (N=10) | Baseline DHEAS >1 SD of Mean Profile 2 (N=18) | Baseline DHEAS at Mean Profile 3 (N=24) | Baseline DHEAS >1 SD of Mean Profile 4 (N=33) | p-value for overall subgroup difference |
|---|---|---|---|---|---|
| D4 (pg/mL) | 1515.1 (1174.0) | 973.2 (446.2) | 927.6 (353.6) | 1180.7 (344.7) | 0.19 |
| D5 (pg/mL) | 865.4 (305.3) | 287.7 (139.1) | 703.6 (327.0) | 1023.8 (366.5) | <0.0001 |
| DHEAS (µg/dL) | 144.6 (49.5) | 43.6 (14.1) | 112.2 (30.2) | 266.1 (44.3) | <0.0001 |
| SHBG (nM) | 46.9 (17.0) | 48.7 (26.1) | 43.3 (22.8) | 52.2 (11.4) | 0.36 |
| T (ng/dL) | 62.7 (22.9) | 34.66 (23.9) | 51.0 (32.4) | 63.0 (24.1) | 0.0088 |
| E2 (pg/mL) | 82.2 (96.3) | 70.9 (73.3) | 59.3 (60.4) | 66.4 (86.9) | 0.28 |
| Cortisol (µg/dL) | 18.3 (6.1) | 13.3 (6.6) | 13.6 (4.0) | 15.3 (3.9) | 0.12 |

Serum concentrations of adrenal related analytes based on the level of DHEAS and related hormones during the menopausal transition.
Reference indicates mean in women with no detectable DHEAS rise during the MT. Other categories represent different DHEAS peaks in women with a rise.

*Figure 4*

Range of values of circulating steroid hormones

- Estradiol
  - 10 to 30 pg/mL
    - 3 Fold
- DS
  - 100- 400 ug/mL
    - 4 Fold
- A-diol
  - <150 - >1,500 pg/mL
    - >10 Fold

E2 and ERLL with lo-med DS

E2 vs ERLL with low DS

*FIGURE 10*

Summation

The findings
- Differences in DS are more substantial than that for other hormones
- A'diol has inherent "estrogenic" bioactivity as shown by ERLL
- A lower B/I ratio indicates that E2 is contributing more to estrogenicity
- Higher DS adds to total "estrogenicity"

The implications
- Individual differences in A'diol are even greater and better define women
- ERLL indicates E2 is supported by other estrogenic compounds
- Subjects with lower E2s and lower DS have a lower B/I ratio
- Increased estrogenicity is provided by A'diol

*FIGURE 11*

Conclusions

- Change in ovarian function triggers an increase in adrenal delta-5 steroids in most, if not all women during the early perimenopause.
- This increase in adrenal delta-5 steroids results in a wide range of circulating A-diol
- Circulating A-diol contributes to the circulating "estrogenicity" in individual women
- It is the adrenal production of steroids...not the ovary... that accounts for between-woman differences in "estrogenicity".
- Tests for estrogen sufficiency should include A-diol

ANDROSTENEDIOL AS AN INDICATOR FOR ASSESSING ESTROGENICITY

CROSS-REFERENCE TO RELATED APPLICATIONS

This application is a U.S. national phase filing under 35 U.S.C. §371 of International Appl. No. PCT/US2010/055967, filed on Nov. 9, 2010, which claims the benefit of U.S. Provisional Application No. 61/259,422, filed on Nov. 9, 2009, the entire contents of both of which are hereby incorporated herein by reference.

FIELD OF THE INVENTION

The present invention provides methods of determining whether a female patient will benefit from hormone replacement therapy.

BACKGROUND OF THE INVENTION

In terms of symptoms and health trajectories associated with the menopausal transition (MT), there is what can be considered a conundrum. This refers to the observation that several deficits and poor health outcomes are related to the menopausal transition and generally resolved by hormone replacement therapy (HRT) but there are no direct causal links or empirical evidence for either the cause or justification of the current intervention therapies. Cognitive and memory loss (as well as many other symptoms) in mid-women is temporally related to declining ovarian function and can be retained by estrogen replacement however, a clear or significant decline in circulating estrogen has not been demonstrated to indicate a deficiency of estradiol at the time of symptom onset. In addition, several reports show that higher endogenous dehydroepiandrosterone (DHEA) safeguards against memory/cognitive loss but an equal number of studies in which DHEA intervention with exogenous DHEA results in no positive effect. In addition, there is no evidence to explain the woman-to-woman difference in symptoms in terms of a difference in a decline of ovarian function that predicts memory/cognitive declines. While women age quite differently . . . they all go through a near-identical change in ovarian function.

So, simply stated: What is it that identifies women who sufferer losses/symptoms from those that do not? To answer this question a large, longitudinal, multicenter clinical study has been carried out. The functional descriptor here is longitudinal because all previous studies were cross-sectional and, as is now understood, the basis for the expression of individual phenotypes during the MT can be recognized only when the same woman is evaluated serially for several years. (Crawford et al., 2009).

Cognitive loss is common among older Americans, approximately twenty percent of the U.S. population is over 60 years of age and this proportion is growing rapidly. The current female:male ratio is 1.3:1 therefore the number of affected women will rise proportionately. Memory and administrative function loss in women is a growing public concern and is a current national health issue. Women are at twice the risk of men for dementia when adjusted for chronologic age (Ott S L, The New York high-risk project: social and general intelligence in children at risk for schizophrenia. Schizophr Res. 1998; 31:1-11; Di Carlo A, Incidence of dementia, alzheimer's disease, and vascular dementia in Italy. The ILSA study. J Am Geriatr Soc. 2002; 50:41-48) and dementia is associated with a large number of other maladies particularly during the menopausal transition. Thus understanding the pathogenesis of cognitive function in mid-aged women has widespread implications for attenuation and prevention of national disease burden. Interventions to prevent memory disorders in women have two historic patterns. One is to follow the observation that hormone replacement therapy (HRT) ameliorates cognitive and administrative function loss, with the conclusion that "estrogen replacement" is therapeutic for maintaining neural function in mid-aged women despite the fact that there is no direct evidence that reduced endogenous estrogen levels are related to the pathogenesis of such cognitive disorders (Goldstein J M, Normal sexual dimorphism of the adult human brain assessed by in-vivo magnetic resonance imaging. Cereb Cortex. 2001; 11(6):490-497; Tobet S A, Hanna I K. Ontogeny of sex differences in the mammalian hypothalamus and preoptic area. Cell Mol Neurobiol. 1997; 17(6):565-601). The second logic is based on observation that higher endogenous circulating dehydroepiandrosterone (DHEA) levels are associated with less cognitive and administrative function loss in mid-aged women (Davis S R, 2008 Dehydroepiandrosterone sulfate levels are associated with more favorable cognitive function in women. J Clin Endocrinol Metab 93:801-808; Haren M T, 2007 Lower serum DHEAS levels are associated with a higher degree of physical disability and depressive symptoms in middle-aged to older African American women. Maturitas 57:347-360) despite the fact that interventions with DHEA have had mixed, at best, results (Barad D, 2007 Update on the use of dehydroepiandrosterone supplementation among women with diminished ovarian function. J Assist Reprod Genet 24:629-634; Kritz-Silverstein D, 2008 Effects of dehydroepiandrosterone supplementation on cognitive function and quality of life: the DHEA and Well-Ness (DAWN) Trial. J Am Geriatr Soc 56:1292-1298). Neither approach is completely effective, based on good science nor deemed to be entirely safe from unwanted somatic side effects.

Despite lacking clinical support, the intervention with estrogen treatment is currently the prevailing therapy for preserving cognitive function in mid-aged women and the risks are considered to out weigh the risks. The overriding question is, does an appropriate replacement therapy that maintains estrogen receptor signal transduction "tone" need to be a pure mitogenic estrogen such as estradiol that carries with it unwanted risks of inducing hyperplastic disease in estrogen-sensitive somatic tissues? Recent observations now indicate this is not true.

ERα in the hippocampus has been associated with learning and memory (Rissman E F., Sex with knockout models: behavioral studies of estrogen receptor alpha. Brain Res. 1999; 835(1):80-90). The secondary estrogen receptor type (ERβ), with poorly defined functions, is also present in the hippocampus, more so in humans than animal models (Shughrue P J, Comparative distribution of estrogen receptor-alpha and -beta mRNA in the rat central nervous system. J Comp Neurol. 1997; 388:507-525). ERα is not only present in inter-neurons but is also found at extra-nuclear sites on dendritic spines and astrocytes near spines, axons forming inhibitory and excitatory synapses. Astrocytes can regulate growth factors, synaptic remodeling and synaptic toss with aging (Zhao L, Estrogen receptor beta s a theraputic target for promoting neurogenesis and preventing neurodegeneration. Drug Dev Res. 2006; 66:103-117). Thus white matter abnormalities may be important in understanding sex differences in vulnerability to memory dysfunction with age, given the role of estrogenic signaling. Androgen receptors (ARs) are also found in the hippocampus but their role has been investigated less but are likely important in promoting an estrogen:androgen balance in neuronal function similar to what is observed in the breast (Toth-Fejel S, Estrogen and androgen receptors as comediators of breast cancer cell proliferation: providing a new therapeutic tool, Arch. Surg. 2004, 139: 50-54; Yeh S, Abnormal mammary gland development and growth retardation in female mice and MCF7 breast cancer cells lacking androgen receptor, J. Exp. Med. 2003, 198: 1899-1908; Agoff S N, Androgen receptor expression in estrogen receptor-negative breast cancer. Immunohisto-chemical, clinical, and prognostic associations, Am. J. Clin. Pathol. 2003, 120: 725-731; Dorgan J F, Relationship of serum dehydroepiandrosterone (DHEA), DHEA sulfate, and 5-androstene-3 beta, 17 beta-diol to risk of breast cancer in postmenopausal women. Cancer Epidemiol Biomarkers Prev. 1997, 6: 177-81). Recent work has mapped the prefronatal cortex and anterior cingulate gyrus (ACG) in animal models to show that androgen receptors are in pyramidal and estrogens receptors are in the non-pyramidal cortical neurons (Garcia-Segura L M, Aromatase expression by astrocytes after brain injury: implications for local estrogen formation in brain repair. Neuroscience. 1999; 89:567-578) with androgen receptors showing associations with excitatory projections and estrogen receptors associated with local inhibitory cortical cells. Thus, estrogen and androgen may have opposing influences on the cortex and neurotransmitter physiology (Kritzer M. The distribution of immunoreactivity for intracellular androgen receptors in the cerebral cortex of hormonally intact adult male and female rats: localization in pyramidal neurons making corticocortical connections. Cereb Cortex. 2004; 14(3): 268-280). Together, this literature suggests important roles for both ERs and ARs in regulating dendritic formation and remodeling and underscores the importance of sex steroid-dependent brain developmental or adult function. More importantly, it suggests that a balance of estrogenic and androgenic inputs may be required for maintaining normal brain function.

Three important findings provide the basis for rethinking the current dogma and unifying our understanding of steroid-dependent deficits in mid-aged women. First of all, it is irrevocably clear that the profound deterioration in cognition in women is linked to the declining ovarian function that all women experience. It is unexplained however how the same decline in ovarian function observed for all women can contribute to such a diverse phenotype with some women severely compromised and others virtually unaffected. It is also abundantly clear that this deterioration in brain function precedes any detectable decline in the production of ovarian steroids but is closely associated with subtle changes that allow follicle stimulating hormone to rise. However, despite this "disconnect" between ovarian steroid hormone production and the onset of neural function decline, intervention with the primary ovarian steroid estradiol (or its congeners) ameliorates and even reverses the functional and behavioral decline that some women experience.

In summary, the efficacy of estrogen treatment indicates that a mechanism at the level of the neuron downstream of the estrogen receptor-signaling process is most likely the "final step" in maintaining optimal neural integrity. However, neither the circulating levels of women requiring estrogen therapy not the adverse systemic responses to exogenous estrogens support the concept that estrogen therapy represents anything similar to an "upstream" physiologic "replacement". Thus the paradox has been that the process of cognitive loss is "caused" by change in ovarian function, as shown by the temporal relationship, and while estrogen treatment is an effective intervention it is clearly not a physiological treatment. So, what else occurs that: 1) parallels the time course of early ovarian function decline, 2) does not have the same qualities in all women, 3) will provide the same intracellular mechanism as estrogens can provide and 4) may explain why higher endogenous levels of DHEA may be beneficial while DHEA intervention has little benefit.

The first of these requirements is met by an observed increase in delta five steroids that occurs at the same trajectory as the phenotypic changes associated with the menopausal transition. The second requirement is met by the observation that while probably all women experience this rise in delta-5 steroids, the individuality of this endocrine event is sufficient to explain woman-to-woman differences in response, phenotype and health outcome. The third and fourth requirements are met by the observation that one of the delta 5 steroids (androstenediol) that are increased during the menopausal transition has both androgenic as well as estrogenic bioactivities. In fact, the observation that higher levels of the delta 5 steroid DHEA are protective for cognition loss, supports the concept that neural integrity is somehow related to this group of adrenal steroid hormones but not necessarily DHEA itself as interventions with this compound alone has had limited success. In sum, the recent recognition of these four aspects of the menopausal transition provides that basis for formulating a new approach to hormone replacement therapy. The present invention provides an approach that is based on the physiological changes that have been shown to occur in mid-aged women and one that fulfills the pharmacologic requirements of "estrogen replacement" indicated by years of intervention and experimentation.

BRIEF SUMMARY OF THE INVENTION

The present invention provides methods of determining whether a female subject will benefit from hormone replacement therapy. Accordingly, in one aspect, the invention provides methods of determining whether a female subject will benefit from estrogenic hormone replacement therapy, comprising determining in a fluid sample from the subject the ratio of total estrogen receptor ligand load (ERLL) to estratriene 3-beta, 17-beta diol (estradiol or E2) in the subject, wherein a ratio of ERLL:E2 in the sample that is below a threshold value indicates that the subject will benefit from estrogenic hormone replacement therapy.

In some embodiments, the threshold value of the ERLL:E2 ratio is 0.65. In some embodiments, the threshold value of the ERLL:E2 ratio is 0.50, 0.51, 0.52, 0.53, 0.54, 0.55, 0.56, 0.57, 0.58, 0.59, 0.60, 0.61, 0.62, 0.63, 0.64, 0.65, 0.66, 0.67, 0.68, 0.69 or 0.70. In some embodiments, the threshold value of the ERLL:E2 ratio is 0.50.

In another aspect, the invention provides methods of determining whether a female subject will benefit from estrogenic hormone replacement therapy, comprising determining in a fluid sample from the subject the circulating concentration of 5-Androstenediol (5A-diol) and the circulating concentration of E2, wherein a circulating concentration of the E2 below 30 pg/ml and a circulating concentration of the 5A-diol below 300 pg/ml indicates that the subject will benefit from estrogenic hormone replacement therapy.

With respect to embodiments of the diagnostic methods, in some embodiments, the fluid sample is blood, plasma or serum. In some embodiments, the concentrations of estrogen receptor ligand load (ERLL) and estratriene 3-beta, 17-beta diol (E2) are measured in a sample taken from the vascular space.

In some embodiments, the estrogenic hormone replacement therapy comprises the administration of an estrogen, for example, a purified conjugated natural estrogen such as equine estrogens (e.g., in combination with a progestin like Premarin), a synthetic estrogen (e.g., ethinyl estradiol), an estradiol in micronized transdermal form, a phytoestrogen, etc.

In some embodiments, the estrogenic hormone replacement therapy comprises the administration of 5 Androstenediol (5A-diol).

In some embodiments, the female subject is perimenopausal, for example, in early or late perimenopause.

In some embodiments, the female subject is postmenopausal, for example, in early or late post menopause.

In some embodiments, the female subject is asymptomatic. In some embodiments, the female subject is exhibiting clinical symptoms of menopause, e.g., increase in fat mass, decrease in muscle mass, osteoporosis, loss of libido, physiological and psychic fatigue, loss of memory, decrease in cognitive functions, etc.

In some embodiments, the female subject is human.

In some embodiments, the methods further comprise the step of administering to the subject a therapeutically effective amount of 5A-diol.

In a related aspect, the invention provides methods of preventing, reducing and/or reversing cognitive deficits in a female subject in need thereof comprising:

a) determining in a fluid sample from the subject the ratio of total estrogen receptor ligand load (ERLL) to estratriene 3-beta, 17-beta diol (E2) in the subject;

b) administering a therapeutically effective amount of the 5A-diol to the patient if the ratio of ERLL:E2 in the sample is below a threshold value.

In some embodiments, the 5A-diol is administered at a dose of at least 30 mg/day.

In some embodiments, the threshold value of the ERLL:E2 ratio is 0.65. In some embodiments, the threshold value of the ERLL:E2 ratio is 0.50, 0.51, 0.52, 0.53, 0.54, 0.55, 0.56, 0.57, 0.58, 0.59, 0.60, 0.61, 0.62, 0.63, 0.64, 0.65, 0.66, 0.67, 0.68, 0.69 or 0.70. In some embodiments, the threshold value of the ERLL:E2 ratio is 0.50.

In some embodiments, the fluid sample is blood, plasma or serum.

In some embodiments, the female subject is perimenopausal, for example, in early or late perimenopause.

In some embodiments, the female subject is postmenopausal, for example, in early or late post menopause.

In some embodiments, the female subject is asymptomatic. In some embodiments, the female subject is exhibiting clinical symptoms of menopause, e.g., increase in fat mass, decrease in muscle mass, osteoporosis, loss of libido, physiological and psychic fatigue, loss of memory, decrease in cognitive functions, etc.

In some embodiments, the female subject is human.

DEFINITIONS

As used herein, the classified the stages of the menopausal transition, are described in Soules, et al., "The Staging of Reproductive Aging in Women: Executive Summary," *Fertility and Sterility* (2001) 76: 874-878.

The term "Premenopause" refers to a time period in a woman's life prior to any age-related change in ovarian function or sex hormone change.

The term "Early Perimenopause" refers to the time period in a woman's life when only non-clinical signs can be observed. For example, a rise in FSH might be observed but no change in ovarian function is observed, and no overt symptoms are observed.

The term "Late Perimenopause" refers to the time period in a woman's life when clinical signs can be observed. For example, changes in menstrual function may be observable.

The term "Menopause" refers to a retrospective time period in a woman's life indicated by one year following a cessation of menstrual periods.

The term "Early post menopause" refers to the time period in a woman's life two years following menopause.

The term "Late post menopause" refers to the time period in a woman's life more than two years following menopause.

The term "androstenediol" or "5A-diol" interchangeably refer to a chemical compound of CAS Registry Number (RN): 521-17-5, having the following chemical structure:

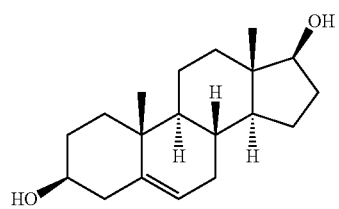

Additional synonyms for 5A-diol include (3-beta,17-beta)-Androst-5-ene-3,17-diol; 3beta,17beta-Dihydroxyandrost-5-ene; 5-AED; Androst-5-ene-3beta,17beta-diol; Androst-5-enediol; EINECS 208-306-8; HE2100; Hermaphrodiol; NSC 12163; UNII-95PS51EMXY; and delta(sup 5)-Androstene-3-beta,17-beta-diol.

BRIEF DESCRIPTION OF THE DRAWINGS

FIG. 3 illustrates mean circulating levels of the relevant hormones during the menopausal transition of the women in SWAN. Groups were defined by the level of DS to determine which hormones changed as DS changed. Note that only androstenediol (5A-diol) changed with DS or showed a statistically significant change.

FIG. 4 illustrates the range of hormone values found during the menopausal transition. Note that estradiol has the least and androstenediol the greatest range. It is the range of androstenediol, but not estradiol concentrations, that best explains the between-women differences seen in symptoms and health outcomes.

FIG. 6 illustrates the determination of E2 and ERLL in women with high DS.

FIG. 7 illustrates the determination of E2 and ERLL in women with high-medium DS.

FIG. 8 illustrates the determination of E2 and ERLL in women with low-medium DS.

FIG. 9 illustrates the determination of E2 and ERLL in women with low DS.

FIG. 10 illustrates a summary of the findings and implications of the present invention.

FIG. 11 illustrates conclusions that are consistent with the present data.

DETAILED DESCRIPTION

1. Introduction

Figure 1:
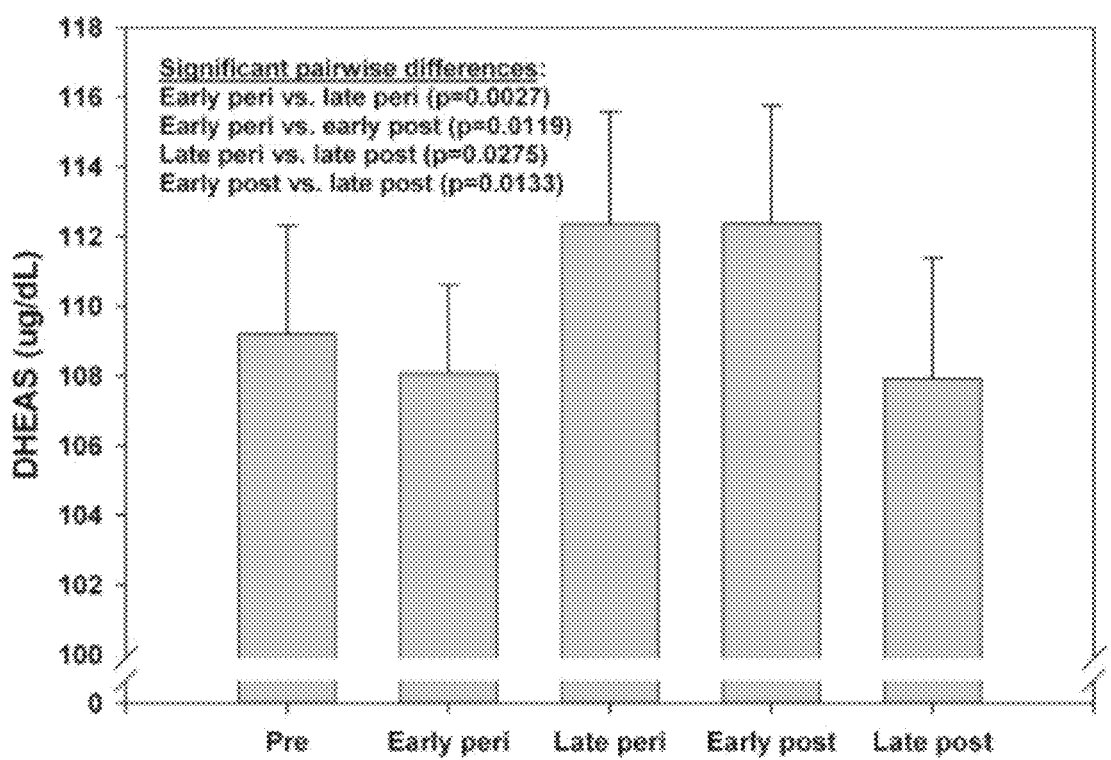
FIG. 1 illustrates the mean levels of circulating DHEA Sulfate (DS) (which is in dynamic equilibrium with DHEA) in all eligible SWAN participants aligned to their ovarian status as they approach menopause. Categories of ovarian status are those defined by WHO and the STRAW convention. This pattern showing a rise in DS as women goes through the menopausal transition. See, Crawford, et al., infra and Soules, et al., supra.

The present invention is based, in part, on the discovery that measuring the relative circulating concentrations of 5-Androstenediol (5A-diol) and estradiol (E2) provides a more accurate determination of whether a female patient will benefit from hormone replacement therapy.

The present invention is also based, in part, on the discovery that some of the benefits that have been previously associated with higher endogenous DHEA in middle-aged women are at least partially attributable to the adrenal secretion of 5A-diol, which is secreted in parallel and is the next steroid in the delta-5 steroidogenic pathway. 5A-diol, which is structurally a C-19 androgen, has inherent estrogenic bioactivity because of the 3-17 diols, and reaches circulating levels that should be considered as effective and contributing to a potential positive endocrine effect for some women. Recent observations indicate that there is a little-recognized rise in DHEA/DHEAS that occurs during the menopausal transition [Lasley et al., *J Clin Endocrinol Metab* (2002) 87:3760-7; and Crawford, et al., *J Clin Endocrinol Metab* (2009) 94(8):2945-51] and this rise is accompanied by a parallel rise in 5A-diol. Longitudinal data from the Study of Women's Health Across the Nation (SWAN) showed that a large majority of middle-aged women exhibited a discernible positive inflection of DHEAS [Lasley, supra] that is not observable when annual measurements of the same DHEAS data are plotted or analyzed according to chronological age [Crawford, supra]. In fact, when the same annual measurements of DHEAS are plotted by chronological age a clear, continuous decline in DHEAS is observed through the fifth decade of life and onward [Crawford, supra]. This dichotomy explains why this phenomenon had been so long overlooked.

Data from the SWAN study further showed that women that had undergone bilateral salpingo-oophorectomy in the early perimenopause exhibit a similar rise in DHEAS in annual samples during the next three to four years. This observation indicates that while the significant changes in circulating sex steroid levels in the perimenopausal transition are triggered by the initial decline in ovarian function during the early perimenopause, the presence of the ovaries are not required to sustain the rise in DHEAS. Furthermore, this observation indicates that some, if not most, of the rise in DHEAS observed at this time is not attributable to ovarian steroidogenesis, but rather to a change in adrenal weak androgen production by the adrenal cortex.

Despite evidence that higher endogenous concentrations of DHEA has substantial benefit in mid-aged women [Davis, et al., *J Clin Endocrinol Metab* (2000) 93:801-808], of the numerous DHEA intervention studies conducted to date, most of these have failed to provide strong or convincing positive evidence [Baulieu et al., *Proc Nat Acad Sci* (2000) 97: 4279-4284; Percheron, et al., *Arch Intern Med* (2003) 163: 720-727] that DHEA or its downstream metabolites are responsible for these benefits. However, metabolic studies following DHEA supplementation indicate that exogenous DHEA is not efficiently converted to the estrogenic compounds that were originally anticipated. In fact, in women, DHEA tends to be converted to bioactive androgens rather than classical bioactive estrogens. The simplest explanation for this paradox is that some of the beneficial effects associated with higher DHEA levels are in some part due to the effects of 5A-diol which is secreted in parallel with DHEA and can provide additional estrogenic support. The dichotomy between the benefits of higher endogenous DHEA and marginal effects of DHEA intervention seem to be that the benefits of high endogenous DHEA is associated with higher 5A-diol in women during the menopausal transition while supplemental exogenous DHEA is not efficiently converted to strong bioactive estrogens.

The SWAN consistently found a modest association between circulating estradiol (E2) and individual phenotypes during the menopausal transition [Randolph, et al., *J Clin Endocrinol Metab* (2003) 88:1516-1522]. One explanation is that classical estrogens are not the only estrogenic hormone contributing to total estrogenicity during the menopausal transition. When the total circulating estrogen alpha receptor ligand load (ERLL) was measured using a cell based bioassay, estradiol (E2) was closely correlated to ERLL while circulating 5A-diol was significantly correlated to ERLL only when E2 concentrations were in the lowest quartile. This observation is consistent with the conclusion that that when E2 levels are reasonable high, E2 concentrations alone are sufficient to maintain an "estrogenized" condition. However, when E2 concentrations are low, then the contribution of non-E2 compounds may be important for an optimal estrogenized condition to exist. When both circulating E2 and 5A-diol concentrations are low, then a poorly-estrogenized condition would more likely exist. Thus, the measurement of circulating 5A-diol, either alone or in combination with E2, more accurately predicts the phenotypes observed during the menopausal transition than measurements of E2 alone.

Circulating concentrations of 5A-diol in some women as they approach and complete the menopausal transition can theoretically contribute as much or more estrogen bioactivity as does E2, depending on how the concentrations of E2 are measured. A recent report indicates that circulating E2 concentrations measured by GC/MS are below 10 pg/mL in some postmenopausal women (Labrie et al., *Menopause* (2010), PMID 20683211). In contrast, circulating concentrations of 5A-diol that can reach concentrations as high as 2,000 pg/mL in the early post menopause could contribute a similar amount or even more estrogenic bioactivity as does E2. Assuming that 5A-diol is not bound as well to sex hormone-binding globulin (SHBG) as E2, the contribution of 5A-diol to tissues could be greater than that of E2 in many women.

Since 5A-diol is not immunoreactive in the current E2 immunoassays that are most frequently used, the 5A-diol component of estrogenicity is not detected or accounted for and the assumption that E2 is the major circulating estrogen is false for some women. The presence of high concentrations of 5A-diol in some women explains why many women do not exhibit the same degree of estrogen deficiency as they traverse the menopausal transition with similar circulating concentrations of E2 as women requiring hormone replacement. Circulating 5A-diol concentrations range from 200-2000 pg/mL and assuming a 5A-diol bioactivity of 5% E2 equivalents, then the contribution of 5A-diol to circulating estrogenicity would easily exceed that of the measured E2 in some women. In women with the lowest circulating 5A-diol (200 pg/mL) the 5A-diol contribution would be 10 pg/mL or less and would not contribute substantially to estrogenic functioning. On the other hand, women with 2,000 pg/mL of circulating 5A-diol, this amount of additional estrogenicity (100 pg/mL of E2 equivalency) would more than triple the average amount of measure E2 in circulation and benefit all women, particularly those with the lowest circulating E2 concentrations.

2. Patients Subject to Diagnosis and Treatment

The methods can be performed on any mammal, for example, a human, a non-human primate, a laboratory mammal (e.g., a mouse, a rat, a rabbit, a hamster), a domestic mammal (e.g., a cat, a dog), or an agricultural mammal (e.g., bovine, ovine, porcine, equine). In some embodiments, the patient is a woman and a human.

Any woman approaching, experiencing or having experienced menopausal transition can benefit from the diagnostic methods of the present invention. For example, in some embodiments, the woman is premenopausal, but post-menarche. In some embodiments, the female subject is perimenopausal, for example, in early perimenopause or late perimenopause. In some embodiments, the female subject is postmenopausal, for example, in early or late post menopause. In various embodiments, the human female subject may be at least 20, 25, 30, 35, 40, 45, 50, 55, 60, 65, 70, 75, 80, 85, 90 years of age, or older.

In some embodiments, the female subject is asymptomatic. In some embodiments, the female subject is exhibiting clinical symptoms of menopause. Relevant clinical symptoms can include without limitation increase in fat mass, decrease in muscle mass, osteoporosis, loss of libido, physiological and psychic fatigue, loss of memory, decrease in cognitive functions, etc.

3. Methods of Diagnosis i. Obtaining a Fluid Biological Sample

In some embodiments, the methods comprise the step of obtaining a fluid biological sample from the subject. The fluid biological sample preferably comprises 5A-diol and/or E2. Illustrative fluid biological samples of use include without limitation, blood, serum, plasma, urine or saliva. The biological sample is obtained in a quantity sufficient for determination of the concentration of 5A-diol and/or E2. Preferably, the biological sample is blood, serum or plasma.

ii. Determining the Ratio of Total Estrogen Receptor Ligand Load (ERLL) to Estratriene 3-Beta, 17-Beta Diol (Estradiol or E2)

The ratio of ERLL to the concentration of E2 in the biological sample ("B/I") can be determined using any method known in the art. Generally, the ERLL and the concentration of E2 are separately determined and then the value of the ERLL is divided by the concentration of E2.

The concentration of estradiol or E2 in a biological sample can be determined using any method known in the art. Methods that find use to quantify E2 include, e.g., high performance liquid chromatography-radioimmunoassay (HPLC-RIA) (Yasui, et al., *Horm Res.* (2004) 61(3):117-25) and GC-MS. Commercial immunoassays for determining the concentration of E2 are available and find use, e.g., from CalBioTech (calbiotech.com); Oxis Intl. (oxisresearch.com); Biosense Laboratories (biosense.com); and Cayman Chemical (caymanchem.com). Other detection and quantification techniques may also find use. See, e.g., the immunoassays described in Lasley et al., *J Clin Endocrinol Metab* (2002) 87:3760-3767 and Crawford et al., *J Clin Endocrinol Metab* (2009) 94(8):2945-51.

The total estrogen receptor ligand load (ERLL) can be determined using any method known in the art. The ERLL provides an estimate of the combined biological potential of the estrogen-alpha receptor ligand load contained in the sample. Cultured cells, for example, human ovarian carcinoma cells that have been stably transfected with a reporter gene plasmid under the regulation of four estrogen-response elements can be used to measure total bioactive estrogens. One example of a useful human ovarian carcinoma cell line is BG1. Other cell lines can find use. The biological sample (e.g., serum) containing estradiol is contacted with the cultured cells containing the reporter gene plasmid and the reporter signal is compared to cultured cells exposed to estradiol standards. The detectable signal of any reporter gene known in the art can be used, including without limitation luciferase and fluorescent proteins (e.g., green fluorescent protein, yellow fluorescent protein, blue fluorescent protein, red fluorescent protein, etc.). In the case where luciferin is used as the reporter gene, luciferin substrate is added to the culture and the luciferase activity induced by the standards and/or test sample are measured using a Luminometer.

The results of the ERLL bioassay are divided by that of the E2 immunoassay (B/I) to generate a dimensionless ratio that conveys the proportion of total E2 equivalents by the measured amount of E2 in a sample. Since E2 has been considered the essential estrogenic component in a serum sample, the B/I ratio indicates what proportion of the total bioactivity is provided by E2. In most women this ratio will be 0.65 or greater, indicating more than half of the "estrogenicity" in a sample is provided by E2. When the ratio falls below 0.5 it indicates that less than half of the biological estrogens are provided by androstenediol.

Subjects having a ratio of ERLL:E2 in the sample that is below a threshold value will benefit from estrogenic hormone replacement therapy. For some subjects having a ratio of ERLL:E2 in the sample that is above the threshold value, estrogenic hormone replacement therapy is not necessary, but the subject may still benefit. In subjects having a ratio of ERLL:E2 in the sample that is sufficiently above the threshold value, estrogenic hormone replacement therapy is not necessary, and the subject is unlikely to benefit.

In some embodiments, the threshold value of the ERLL:E2 ratio is 0.65. In some embodiments, the threshold value of the ERLL:E2 ratio is 0.50, 0.51, 0.52, 0.53, 0.54, 0.55, 0.56, 0.57, 0.58, 0.59, 0.60, 0.61, 0.62, 0.63, 0.64, 0.65, 0.66, 0.67, 0.68, 0.69 or 0.70. In some embodiments, the threshold value of the ERLL:E2 ratio is 0.50. For subjects having a ratio of ERLL:E2 that is in the range of about 0.65-0.75, e.g., 0.66, 0.67, 0.68, 0.69, 0.70, 0.71, 0.72, 0.73, 0.74, 0.75, estrogenic hormone replacement therapy is not necessary, but the subject may still benefit. For subjects having a ratio of ERLL:E2 that is above 0.75, estrogenic hormone replacement therapy is not necessary, and the subject is unlikely to benefit.

iii. Determining the Concentration of 5-Androstenediol (5A-Diol) and/or Estradiol (E2)

In various embodiments, the methods comprise determining the concentration levels in the biological sample of 5A-diol alone or in conjunction with concentration levels of E2, or the ERLL:E2 ratio.

The concentration in the biological sample of 5A-diol can be determined using any method known in the art. Methods that find use to quantify 5A-diol include, e.g., gas chromatography-mass spectrometry (GC-MS) (Hill, et al., *J Steroid Biochem Mol Biol.* (2005) 96(2):187-200; and Tagawa, et al., Steroids (2004) 69(10):675-80); liquid chromatography-mass spectrometry (LC-MS) (Mizokami, et al, *Cancer Res.* (2004) 64(2):765-71); and enzyme immunoassay (EIA) (Tagawa, *Clin Chim Acta.* (2000) 296(1-2):193-201). Other detection and quantification techniques may also find use. See, e.g., the immunoassays described in Lasley, et al., *J Clin Endocrinol Metab* (2002) 87:3760-3767 and Crawford et al., *J Clin Endocrinol Metab* (2009) 94(8):2945-51.

Circulating 5A-diol concentrations can range from 200-2000 pg/mL in women during the menopausal transition and immediately after. A circulating concentration of 5A-diol below a predetermined threshold concentration indicates that the subject will benefit from estrogenic hormone replacement therapy; therefore estrogenic hormone replacement therapy is recommended. A circulating concentration of 5A-diol above the predetermined threshold concentration indicates that the subject does not need, although may benefit, from estrogenic hormone replacement therapy. The threshold level for 5A-diol can be in the range of about 300 pg/mL to about 500 pg/mL. In various embodiments, the predetermined threshold level for a circulating concentration of 5A-diol is 300 pg/mL, 325 pg/mL, 350 pg/mL, 375 pg/mL, 400 pg/mL, 425 pg/mL, 450 pg/mL, 475 pg/mL, or 500 pg/mL. In certain embodiments, the threshold level for 5A-diol is 300 pg/mL.

In various embodiments, the concentration of 5A-diol and the concentration of E2 are determined in the biological sample. The concentration in the biological sample of estradiol can be determined using any method known in the art, as described herein.

Circulating E2 concentrations can range from <10 pg/mL to 200 pg/mL. A circulating concentration of E2 below a predetermined threshold concentration indicates that the subject will benefit from estrogenic hormone replacement therapy; therefore estrogenic hormone replacement therapy is recommended. A circulating concentration of E2 above the predetermined threshold concentration indicates that the subject does not need, although may benefit, from estrogenic hormone replacement therapy. When determining the E2 concentration by immunoassay, the threshold level for E2 can be in the range of about 30 pg/mL to about 50 pg/mL. In various embodiments, the predetermined threshold level for a circulating concentration of E2 is 30 pg/mL, 35 pg/mL, 40 pg/mL, 45 pg/mL, or 50 pg/mL. In certain embodiments, the threshold level for E2 is 30 pg/mL. When determining the E2 concentration using mass spectrometry methods, the threshold level will be relatively lower.

The circulating concentration of 5A-diol and/or E2 in a subject can be determined one or more times, as appropriate or desired. For example, the circulating concentration of 5A-diol and/or E2 may be determined one a year, once every two years or once every three years, or more or less often, as appropriate. As appropriate, determinations may be carried out on a biological sample from a subject who is premenopausal, perimenopausal or postmenopausal. Determinations may need to be more frequent in a patient who is symptomatic of menopausal symptoms or who is receiving estrogenic hormone replacement therapy. In such instances, determinations may be performed once monthly, once every two months, once every three months, or twice yearly, as appropriate.

iv. Providing Diagnosis and/or Therapy to Patient

In some embodiments, the methods further comprise the step of providing the diagnosis and/or recommendation to the subject of whether or not they would benefit from a therapeutic regime of estrogenic hormone replacement therapy, based on an analysis of the results obtained of determining the concentration of 5A-diol, E2 and/or the ERLL:E2 ratio in the biological sample.

In some embodiments, the methods further comprise the step of administering to the subject a therapeutic regime of estrogenic hormone replacement therapy. Established estrogenic hormone replacement therapies are known in the art and find use. In some embodiments, the estrogenic hormone replacement therapy comprises the administration of an estrogen, for example, a purified conjugated natural estrogen such as equine estrogens (e.g., in combination with a progestin like Premarin), a synthetic estrogen (e.g., ethinyl estradiol), an estradiol in micronized transdermal form, a phytoestrogen, etc.

In some embodiments, the estrogenic hormone replacement therapy comprises the administration of 5 Androstenediol (5A-diol). In some embodiments, the estrogenic hormone replacement therapy comprises the administration of 5 Androstenediol (5A-diol) and an estrogen.

5 Androstenediol (5A-diol) can be formulated for delivery by any appropriate route of administration to achieve a therapeutically effective dose. Illustrative routes include without limitation oral, sublingual, buccal, subcutaneous and transdermal. A therapeutically effective dose is one that achieves the therapeutically desired effect (e.g., reduction or elimination of symptoms associated with the menopausal transition), with minimal or no undesirable side effects. A trained clinician can readily determine an appropriate dosage for an individual patient, for example, by starting at a low dose and then incrementally increasing over time until a desired therapeutic effect is achieved with minimal or no undesirable side effects. The actual dose for an individual patient will depend on several factors, including the age, weight, menopausal status (e.g., premenopausal, perimenopausal, postmenopausal), and general health of the patient. Therapeutically effective doses for 5A-diol are generally in the range of about 5 mg/day to about 30 mg/day, for example, about 5 mg/day, 10 mg/day, 15 mg/day, 20 mg/day, 25 mg/day or 30 mg/day.

Compositions comprising 5A-diol contain an effective amount of 5A-diol in admixture with pharmaceutically acceptable carriers and excipients. The compositions can be in the form of unitary dosages suitable for the administration of up to 30 mg of 5A-diol, for example, a unitary dose of about 5 mg, 10 mg, 15 mg, 20 mg, 25 mg or 30 mg. The dosage units can be single or subdivided in the therapeutic daily dose.

Illustrative pharmaceutical compositions include tablets, capsules, pills, solutions, syrups, injectable forms, topical forms such as creams or ointments, or transdermal formulations, known in the art.

In various embodiments, compositions comprising therapeutically effective amounts of 5A-diol and estradiol are provided.

4. Methods of Reducing or Inhibiting Cognitive Deficits in a Subject

The invention further provides methods of preventing, reducing and/or reversing cognitive deficits and/or improving cognitive abilities in a female subject in need thereof comprising first determining in a fluid sample from the subject the ERLL:E2 ratio or the concentration levels of 5A-diol and E2, as described above. If it is determined that the ERLL:E2 ratio and or the 5A-diol and E2 concentration levels are below a threshold value, as described above, a therapeutically effective amount of the 5A-diol is then administered to the patient.

The administered dose of 5A-diol is an amount sufficient to prevent, reduce and/or reverse cognitive deficits and/or improve cognitive abilities in the female subject. Applicable doses of 5A-diol are described herein. In some embodiments, higher doses of 5A-diol are administered in order to reduce and/or reverse cognitive deficits and/or improve cognitive abilities than the doses that would be administered for estrogenic hormone replacement therapy. For example, in some embodiments, doses of 5A-diol greater than 30 mg/day, e.g., 30 mg/day, 35 mg/day, 40 mg/day, 45 mg/day or 50 mg/day, are administered in order to reduce and/or reverse cognitive deficits and/or improve cognitive abilities.

Objective parameters for determining cognitive abilities in a subject are known in the art and find use. Cognitive abilities can be measured using any method known in the art. One test is the mini mental state examination (MMSE) (Folstein, et al., *Journal of Psychiatric Research* 12 (3): 189-98). Subjects who maintain the same score or who achieve a higher score on an MMSE indicate that the treatment or prevention regime is efficacious. Conversely, subjects who score lower on an MMSE indicate that the treatment or prevention regime has not been efficacious.

Subjects amenable to treatment may have age-associated memory impairment (AAMI), or mild cognitive impairment (MCI). MCI, also known as incipient dementia, or isolated memory impairment) is a diagnosis given to individuals who have cognitive impairments beyond that expected for their age and education, but that do not interfere significantly with their daily activities. Petersen, et al., *Arch. Neurol.* (1999) 56 (3): 303-8. MCI is diagnosed when there is: (1) evidence of memory impairment; (2) preservation of general cognitive and functional abilities; and (3) absence of diagnosed dementia. Morris, et al., *Arch. Neurol.* (2001) 58 (3): 397-405. Cognitive assessment tests used for diagnosing AAMI, MCI or Alzheimer's disease can be used to test for cognitive deficits in female subjects experiencing menopausal transition, as well as for monitoring improvements or reductions in cognitive abilities.

Baseline evaluations of patient function can made using classic psychometric measures, such as the Mini-Mental State Exam (MMSE) (Folstein, et al., supra), and the Alzheimer's Disease Assessment Scale (ADAS), which is a comprehensive scale for evaluating patients with Alzheimer's Disease status and function. Rosen, et al., *Am J Psychiatr* (1984), 141:1356-1364. These psychometric scales provide a measure of cognitive function and are useful for monitoring improvements or reductions in cognitive abilities. Suitable qualitative life scales can also be used to monitor treatment. The extent of disease progression can be determined using a Mini-Mental State Exam (MMSE). Folstein, et al., *Journal of Psychiatric Research* 12 (3): 189-98. Any score greater than or equal to 25 points (out of 30) is effectively normal (intact). Below this, scores can indicate severe ($\leq 9$ points), moderate (10-20 points) or mild (21-24 points) disease.

A baseline psychometric assessment can be made prior to commencing a therapeutic regime of 5A-diol, and then follow-up psychometric assessments can be made to determine if the cognitive abilities of the patient further deteriorate, stabilize or improve. Follow-up psychometric assessments can be made monthly, every two, three, four or six months, or annually, as necessary or appropriate. If an improvement or stabilization in cognitive abilities is observed, the therapeutic regimen 5A-diol may be continued at the same dose, assuming no undesirable side effects are experienced. If a reduction in cognitive abilities is observed, the therapeutic regimen 5A-diol may be continued at a higher dose, assuming no undesirable side effects are experienced. If the therapeutic regimen of 5A-diol still does not improve or stabilize cognitive abilities, or if undesirable side effects are observed, the therapeutic regimen of 5A-diol should be discontinued.

EXAMPLES

The following examples are offered to illustrate, but not to limit the claimed invention.

Example 1

Materials and Methods

Thirty-five hundred mid-aged women were studied over eleven years in a cooperative agreement under NIA. In this study of Women Across the Nation (SWAN), annual blood samples were collected and used for hormone analysis. All hormones relevant to this report are found in two previous reports (See, Lasley et al., 2002 and Crawford et al., 2009). Briefly, estradiol (E2), testosterone (T), dehydroepiandrosterone sulfate (DS), androstenediol (5A-diol), androstendione (A-dione), follicle stimulating hormone FSH), luteinizing hormone (LH) were measured by previously validated immunoassay (Lasley et al., 2002 and Crawford et al., 2009).

Biological-to-Immunological (B/I) Ratio

Immunoassay (for Estradiol, E2):

Any of several commercial immunoassays for E2 can be used for this measurement. Concentrations of serum E2 are common although different final results will be obtained with different assay formats. The measurement of E2 by immunoassay provides an "immunoactive" or mass concentration. In the current procedure, an automated platform (ACS-180) was used. Briefly, this assay uses estradiol labeled with DMAE, a polyclonal rabbit anti-estradiol antibody, and a monoclonal mouse anti-rabbit antibody coupled to PMP. Serum is required for the assay in addition to sufficient dead volume for aspiration and repeat assay determinations. If other immunoassays are used which have different performance characteristics, then the threshold ratio cut-off limits will need to be established.

Estrogen Receptor Bioassay:

This assay assesses the total estrogenic bioactivity contained in a serum sample. Thus and estimate of the combined biological potential of the estrogen-alpha receptor ligand load (ERLL) contained in the sample. Thus the bioactivity of a sample will be appropriately estimated. Briefly, human ovarian carcinoma cells (BG1) that have been stably transfected with a luciferase reporter gene plasmid under the regulation of four estrogen-response elements were used to measure total bioactive estrogens. BG1 cells were cultured in Alpha Minimum Essential Medium (Alpha-MEM) with 10% fetal bovine serum (FBS). When cells reached 80% confluence, cells were trypsinized (0.05% trypsin-EDTA) and well dispersed in phenol-red free Dulbecco's Minimum Essential Medium (DMEM) supplemented with 10% dextran charcoal treated FBS (DCC-FBS). Suspended cells (0.05 mL/well; density of 25,000 cells/0.05 mL) were added to 96-well tissue culture plates containing 0.15 mL/well of phenol-red free DMEM supplemented with 10% DCC-FBS. On each of the two subsequent days (Days 2 and 3), the media in each well was removed and replaced with 0.2 mL phenol-red free DMEM supplemented with 10% DCC-FBS. On Day 4, media was again removed and replaced with 0.2 mL phenol red-free DMEM supplemented with 10% DCC-FBS containing increasing concentrations of estradiol (E2) standards or sample sera. Estradiol standards were dissolved in ethyl alcohol and had a final alcohol content of 0.1% (v/v) to minimize any organic solvent effects. To compensate for any serum matrix effects, DCC-FBS was added to the E2 standard preparation at a proportion equal to that of the serum content of the sample preparation (5% v/v). Serum samples were diluted in DCC-FBS with a final serum content of 5% (v/v). Plates were then incubated for an additional 18 hours. Media was then removed and 0.1 mL cell lysis buffer added to each well and allowed to incubate for 20 minutes. Cell lysates (0.04 mL) were transferred to 96-well Microfluor II plates (Fisher Scientific, Santa Clara, Calif.). Luciferin substrate was injected into each well and the luciferase activity induced by the standards and/or test serum was measured by a Veritas Luminometer (Turner Biosystems, Sunnyvale, Calif., USA).

The final step is to divide the result of the bioassay by that of the immunoassay (B/I) to generate a dimensionless ratio that conveys the proportion of total E2 equivalents by the measured amount of E2 in a sample. Since E2 has been considered the essential estrogenic component in a serum sample, the B/I ratio indicate what proportion of the total bioactivity is provided by E2. In most women this ratio will be 0.65 or greater, indicating more than half of the "estrogenicity" in a sample is provided by E2. When the ratio falls below 0.5 it indicates that less than half of the biological estrogens are provided by androstenediol.

Results:

The foundational elements for understanding the value of adrenal steroid hormones and specifically 5A-diol as a marker for estrogen balance stems from two previous reports. The first of these reports is that of Lasley et al (2002) which indicated that adrenal function in mid-aged women undergoes a positive inflection as menopause approaches. This report represented a paradigm shift in the study of the menopause. The second, Crawford et al., 2009) confirmed the earlier report with additional data and demonstrated that most (85%) of mid-aged women exhibited a rise in DS between early peri-menopause and early post-menopause. This new finding represents a research shift away from the ovary towards the adrenal.

Figure 2:
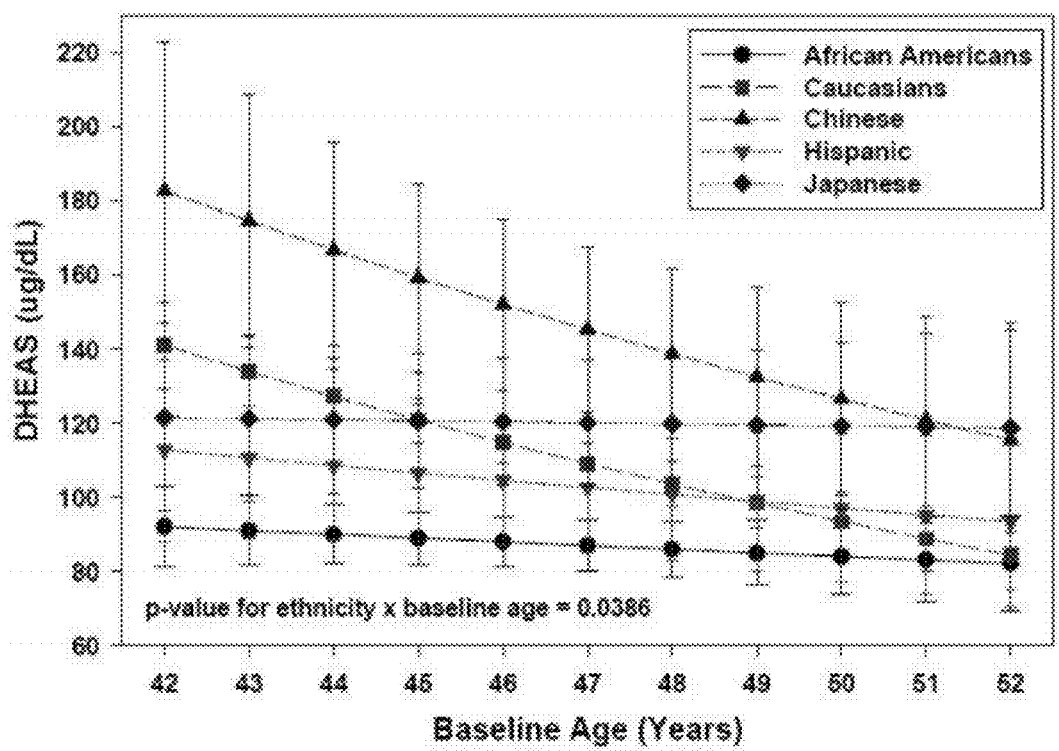
FIG. 2 illustrates the same DS data as shown in FIG. 1 except aligned by chronological age. This is the pattern that all previous studies had indicated and could not be rectified until longitudinal data were made available through the SWAN. The patterns shown in this figure are the currently accepted dogma.

The rise in DS (FIG. 1) was not previously appreciated because all previous studies of mid-aged women were cross-sectional rather than longitudinal (FIG. 2). Thus, the importance of changes in ovarian hormone production shifts to gaining a better understanding of adrenal hormone changes during the menopausal transition.

The second element in developing the current concept came as a result of probing deeper into the inflection of circulating DS just prior to menopause. When the attendant hormones were analyzed (i.e., T, A-dione, 5A-diol, T and E2) were measured and analyzed, it became clear that A-diol not only tracked DS with a correlation coefficient of near 0.9 but revealed a greater fold-increase than any of the other hormones of interest (FIG. 3, 5A-diol shown as D5). In comparison A-diol ranges over a ten-fold range which is much greater that that of estradiol or DS (FIG. 4).

Figure 5:
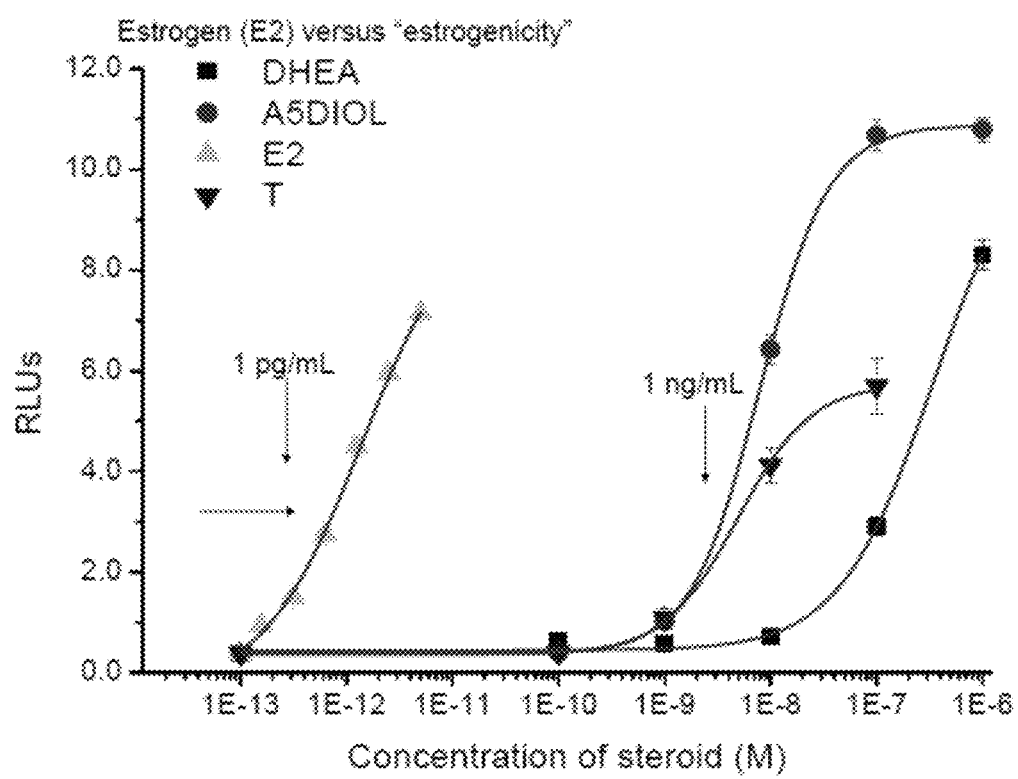
FIG. 5 illustrates a dose-response curves for DHEA, androstenediol (5A-diol) estradiol (E2) and testosterone (T) using a cell-based bioassay to determine estrogenic effects (estrogenicity). Note that androstenediol had significant "estrogenicity" at physiological levels (arrow) while DHEA does not. Such data have not previously been reported.
Figure 6:
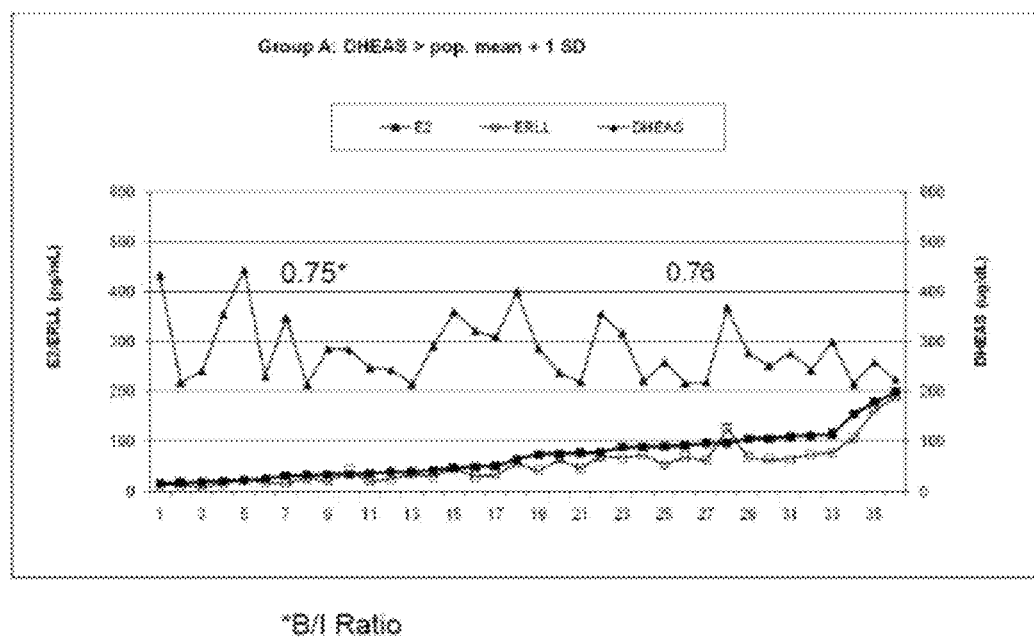
FIGS. 6-9 illustrate circulating levels for individual women divided into groups according to the DS levels. Each panel also shows the corresponding estradiol (E2) level arranged from lowest on the left to the highest on the right for each category. Total estrogenicity (ERLL) was also measured. The ratio of the ERLL divided by the E2 concentration is shown for low and high E2 levels in each panel. Note that only when both E2 and DS are low does the ratio fall below 0.5. The E2 assay uses estradiol labeled with DMAE, a polyclonal rabbit anti-estradiol antibody, and a monoclonal mouse anti-rabbit antibody coupled to PMP. At least about 45 µL of serum is used for the assay in addition to sufficient dead volume for aspiration and repeat assay determinations. The SWAN reporting range for the estradiol assay is 10 to 200 pg/mL.
Figure 7:
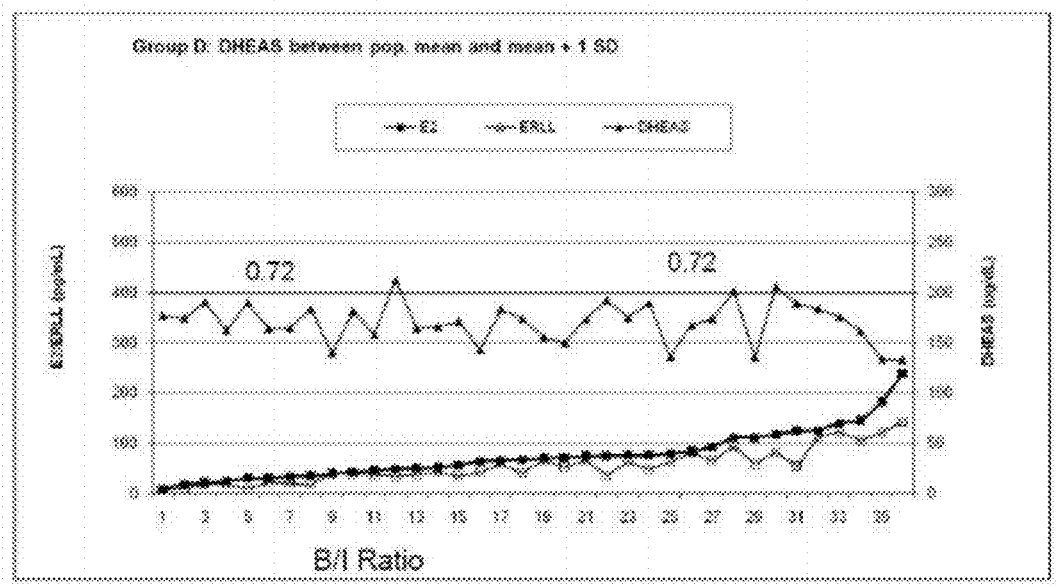
Figure 8:
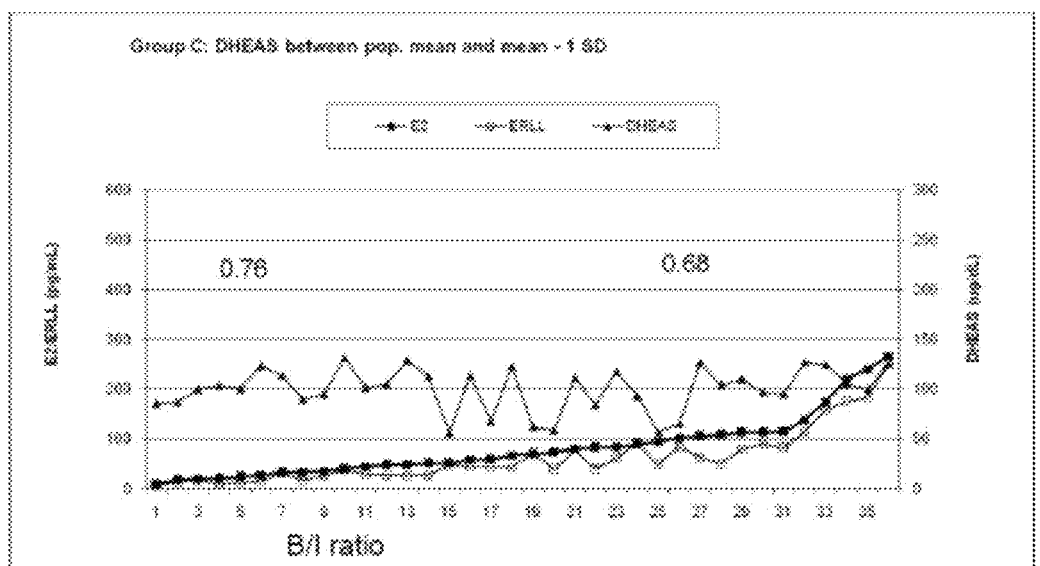
Figure 9:
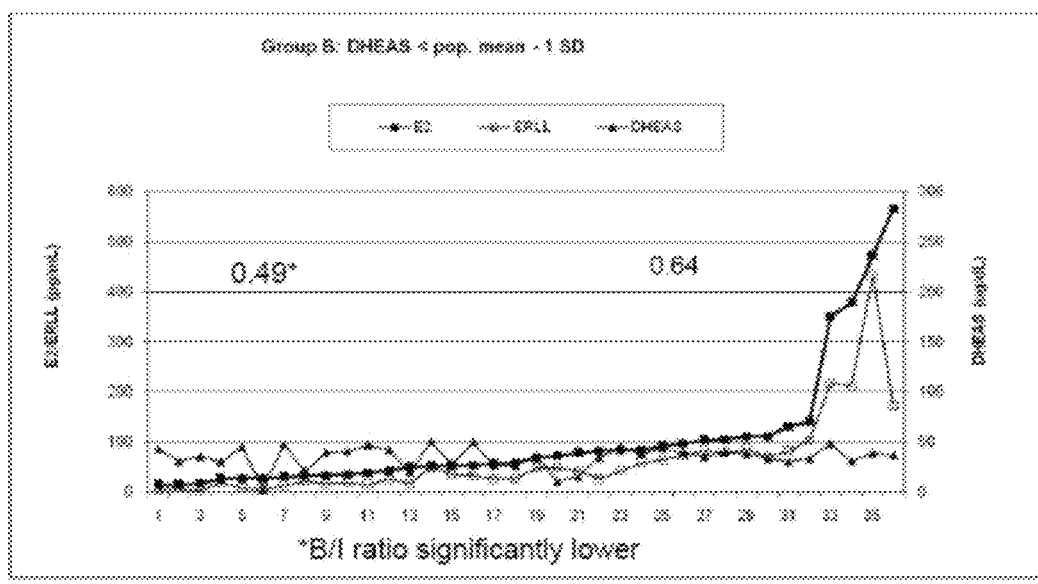

The third element for developing the concept was that of gaining additional insight into the innate properties of all of the adrenal steroids that were associated with the rise of DS during the menopausal transition. For these investigations newly developed in vitro bioassays were used to adjudicate the estrogenicity of all for adrenal steroids (i.e., T, A-dione, 5A-diol and DHEA). These investigations revealed that only 5A-diol and estradiol had substantial inherent estrogenic bioactivity at their physiological circulating concentrations (FIG. 5).

The final element of the concept was the result of asking the direct question of the contribution of E2 versus adrenal steroid hormones to total estrogenic bioactivity by measuring the total estrogen receptor ligand load (ERLL) which is referred to herein as "estrogenicity". In this portion of the study samples were selected that represented women with "high" (FIG. 6), "high-medium" (FIG. 7), "low-medium" (FIG. 8) and "low" (FIG. 9) DS and then divided between "low" (first 16 values) and "high" (second 16 values) of E2 for each of the four DS categories and were then evaluated for ERLL. The concentration of ERLL was then divided by the concentration of E2 to generate and B/I ratio (inset in each of the four panels) which reflected the contribution of E2 to the ERLL or "estrogenicity". The results of these measurements reveal that in all but one category, the contribution of E2 to ERLL was 0.64 or higher, thus indicating that E2 was the predominate estrogen contributing to the more general estrogenicity. However, in the group where both E2 and DS were low (FIG. 9), the E2/ERLL ratio dropped below 0.5 indicating E2 was not the primary contributor to estrogenicity and that contributions from adrenal steroids were a primary contributor to ERLL (FIGS. 6-9).

Discussion:

The interpretation of these new data requires a step-wise evaluation of the separate components. First, the SWAN study shows that while all women are strikingly similar in terms of their change in the production of ovarian hormones, they are strikingly different in terms of adrenal hormone production. This new understanding explains the first part of the conundrum ... "why do women express such a wide range of phenotypes when their change in ovarian function is not so different"? The short answer is, because the primary hormonal difference between women is not the difference in ovarian hormone production but a difference in adrenal hormone production. The second revelation is that adrenal hormone production can add substantially to a woman's total estrogenicity. Higher adrenal contribution adds estrogenic compounds to the circulation. Since both ovarian and adrenal estrogens act though the same pathways at the level of cell function, the replacement of "estrogen", in any form can resolve an estrogen deficiency if it exists. This answers the second part of the conundrum . . . "how are current HRT effective if lower estradiol cannot be established?" The short answer here is that if enough adrenal estrogenic compounds are produced then estrogen deficiency is less likely to occur even in the face of low estradiol production by the ovary. Finally, if adrenal hormones are in fact the missing element in the menopausal transition (MT) deficiencies, then why doesn't supplementation with DHEA resolve these deficits? There is no short answer here but contrary to the current/past dogma, it seems that DHEA (which is not estrogenic) is not efficiently converted to A-diol which is estrogenic. Simply stated . . . the wrong compound was used in all of the intervention studies.

Several intervention studies showing limited positive effects of DHEA supplementation are in conflict with the concept that marked benefits are attributed to higher endogenous circulating DHEA levels (Davis et al., 2008). This is consistent with the positive effects actually reflecting the parallel increased in endogenous A-diol and DS as shown here. Oral DHEA (50 mg/day) taken by men and women for one year was shown to modestly decrease bone turnover, increase libido and improve skin hydration in women over 70 years old. These effects indicated that DHEA supplementation normalized some effects of aging without dramatic improvements in general health (Baulieu et al., 2000).

Similarly, a one-year study of men and women between 60 and 80 years of age taking 50 mg/day oral DHEA revealed no positive effect on muscle status in health subjects (Parcheron et al., 2003). More recently, a larger study of adults 55-85 years of age taking 50 mg daily, oral DHEA revealed only modest effect of BMD and bone resorption in women but not men (von Muhlen et al., 2008). While local DHEA, administered as an intravaginal suppository, provided a highly efficient treatment of age-related vaginal atrophy (Labrie et al., 2009a) with no significant change in circulating sex steroid concentrations (Labrie et al., 2009b). Transdermal administration of DHEA to 60-65 year old women led to a five fold increase in circulating DS but less than a two and one-half fold increase in circulating androstendiol glucuronides (Labrie et al., 2007) and a 25 mg oral dose for three months resulted in a doubling of circulating concentrations of A-diol (0.32 to 0.66 ng/mL (Stanczyk et al., 2009) suggesting that peripheral conversion of exogenous DHEA to A-diol is relatively modest. In contrast, the rise in circulating A-diol can be greater than five-fold in some women (<0.3 to >1.5 ng/mL) during the menopausal transition as DS levels rise from early peri- to early late peri-menopause (FIG. 1). Taken together, these and the present report suggests that the positive association of endogenous circulating DHEA to superior health outcomes may be explained by the strong positive association of a rise of A-diol with increased DS and DHEA. Thus increased circulating A-diol levels with its inherent estrogenic activity and not DHEA may be primarily responsible for most of the positive physiological effects.

SUMMARY

A longitudinal study of mid-aged women approaching menopause shows that individual differences in hormone production is largely attributed to the adrenal rather than the ovaries. Subsequent studies show that one of the adrenal hormones has inherent estrogenic bioactivity. Women who have a lower adrenal response and lower ovarian estrogen production have significantly lower estrogenicity (FIG. 10) and would be candidates for HRT.

CONCLUSION

Identifying women who will require HRT for symptoms of the MT require the measurement of 5A-diol or its direct metabolites (FIG. 11).

REFERENCES

Baulieu E E, Thomas G, Legrain S, Lahlou N, Roger M, Debuire B, Francounau G, Hervy M-P, Latour F, Leaud M-C, Mokrane A, Pitti-Ferrandi, Trivalle C, de Lacharriere O, Nouveau S, Rakoto-Arison B, Souberbielle J-C, Raison J, Raynaud A, Girerd X, Forette F. 2000, Dehydroepiandrosterone (DHEA, DHEA sulfate, and aging: Contribution of the DHEAge Study to a sociobiomedical issue. Proc Nat Acad Sci 97: 4279-4284.
Crawford, S., Santoro, N., Laughlin, G. A., Sowers, M. F., McConnell, D., Sutton-Tyrrell, K., Weiss, G., Vuga, M., Randolph, J., and Lasley, B. L., 2009, Circulating Dehydroepiandrosterone Sulfate Concentrations during the Menopausal Transition. J Clin Endocrinol Metab 94(8): 2945-51.
Davis S R, Shah S M, McKenzie D P, Kulkarni J, Davison S L, Bell R J. 2008 Dehydroepiandrosterone sulfate levels are associated with more favorable cognitive function in women. J Clin Endocrinol Metab 93:801-808.
Labrie F, Archer D, Bouchard C, Fortier M, Cusan L, Gomez J L, Girard G, Baron M, Ayotte N, Moreau M, Dube R, Cote I, Labrie F, Berger L, Gilbert L, Martel C, Baiser J. 2009a, Menopause. 16(5):907-922.
Labrie F, Archer D, Bouchard C, Fortier M, Cusan L, Gomez J L, Girard G, Baron M, Ayotte N, Moreau M, Dube R, Cote I, Labrie F, Berlanger P, Berger L, Gilbert L, Martel C, Baiser J. (2009b). Serum steroid levels during 12 week intravaginal dehydropiandrosterone administration. 16(5): 897-906.
Labrie F, Berlanger A, Berlanger P, Berube R, Martel C, Cusan L, Gomez J L, Candas B, Chaussade V, Castiel I, Deloche C, Leclaire J. (2007) Metabolism of DHEA in postmenopausal women following percutaneous administration. J Steroid Biochem Mol Biol 103(2): 178-188.
Lasley B L, Santoro N, Randolf J F, Gold E B, Crawford S, Weiss G, McConnell D S, Sowers M F 2002 The relationship of circulating dehydroepiandrosterone, testosterone, and estradiol to stages of the menopausal transition and ethnicity. J Clin Endocrinol Metab 87:3760-3767
Percheron G, Hogrel J-Y, Denot-Ledunois S, Fayet G, Forette F, Baulieu E E, Fardeau M, Marini J-F. 2003, Effect of a 1-year oral administration of dehydroepiandrosterone to 60-to-80 year-old individuals on muscle function and cross-sectional area. Arch Intern Med 163: 720-727.
Stanczyk F Z, Slater C C, Ramos D E, Azen C, Cherala G, Hakala R Ph, Abraham G, Roy S. 2009, Pharmacokinetics of dehydroepiandrosterone and its metabolites after long-term oral dehydroepiandrosterone treatment in postmenopausal women. Menopause 16(2): 272-278.
Von Muhlen D, Laughlin G A, Kritz-Silverstein D, Bergstrom J, Bettencourt R. 2008, Effect of dehydroepiandrosterone supplementation on bone mineral density, bone markers and body composition in older adults. Osteoporos Int. 19(5): 699-707.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:
1. A method of determining whether a female subject will benefit from estrogenic hormone replacement therapy, comprising:
 a) determining in a fluid sample from the subject the the circulating concentration of 5-Androstenediol (5A-diol); and
 b) providing a regimen of estrogenic hormone replacement therapy when the circulating concentration of the 5A-diol in the sample is below a threshold value.
2. The method of claim 1, wherein the threshold value is a circulating concentration of 300 pg/ml 5A-diol.
3. The method of claim 1, wherein the fluid sample is blood, plasma or serum.
4. The method of claim 1, wherein the estrogenic hormone replacement therapy comprises the administration of an estrogen.
5. The method of claim 1, wherein the female subject is perimenopausal or postmenopausal.

6. The method of claim 1, wherein the female subject is asymptomatic.

7. The method of claim 1, further comprising the step of administering to the subject a therapeutically effective amount of an estrogen.

8. A method of determining whether a female subject will benefit from estrogenic hormone replacement therapy, comprising:
   a) determining in a fluid sample from the subject the circulating concentration of 5A-diol and the circulating concentration of E2; and
   b) providing a regimen of estrogenic hormone replacement therapy when the circulating concentration of the E2 is below 30 pg/ml and the circulating concentration of the 5A-diol below 300 pg/ml.

9. The method of claim 8, wherein the fluid sample is blood, plasma or serum.

10. The method of claim 8, wherein the estrogenic hormone replacement therapy comprises the administration of an estrogen.

11. The method of claim 8, wherein the female subject is perimenopausal or postmenopausal.

12. The method of claim 8, wherein the female subject is asymptomatic.

13. The method of claim 8, further comprising the step of administering to the subject a therapeutically effective amount of an estrogen.

14. The method of claim 1, wherein the female subject is human.

15. The method of claim 1, wherein the female subject is exhibiting symptoms of menopause.

16. A method of determining whether a female subject will benefit from estrogenic hormone replacement therapy, comprising:
   a) determining in a fluid sample from the subject the circulating concentration of 5-Androstenediol (5A-diol) in the subject; and
   b) providing a regimen of estrogenic hormone replacement therapy when the circulating concentration of the 5A-diol in the sample is outside the range of from 200-2000 pg/mL.

17. The method of claim 16, wherein the fluid sample is blood, plasma or serum.

18. The method of claim 16, wherein the estrogenic hormone replacement therapy comprises the administration of an estrogen.

19. The method of claim 16, wherein the female subject is perimenopausal or postmenopausal.

20. The method of claim 16, wherein the female subject is asymptomatic.

21. The method of claim 16, wherein the female subject is exhibiting symptoms of menopause.

22. The method of claim 16, further comprising the step of administering to the subject a therapeutically effective amount of an estrogen.

23. The method of claim 16, wherein the female subject is human.

* * * * *